United States Patent [19]

May

[11] Patent Number: 4,458,367

[45] Date of Patent: Jul. 10, 1984

[54] KNEE JOINT FOR ARTIFICIAL LIMBS

[75] Inventor: Denis R. W. May, London, England

[73] Assignee: J. E. Hanger & Company Limited, London, England

[21] Appl. No.: 386,454

[22] Filed: Jun. 8, 1982

[30] Foreign Application Priority Data

Jun. 9, 1981 [GB] United Kingdom ................ 8117573
Jun. 9, 1981 [GB] United Kingdom ................ 8117574

[51] Int. Cl.³ .............................................. A61F 1/04
[52] U.S. Cl. .............................................. 3/22; 3/27; 3/26
[58] Field of Search ................ 3/2, 6, 6.1, 26, 27, 3/22, 21, 28

[56] References Cited

U.S. PATENT DOCUMENTS

| Re. 22,903 | 8/1947 | Hinkle | 3/2 |
|---|---|---|---|
| 795,734 | 7/1905 | Seeley | 3/2 |
| 3,920,610 | 11/1975 | Wagner | 3/6.1 |
| 4,023,215 | 5/1977 | Moore | 3/26 |
| 4,283,800 | 8/1981 | Wilson | 3/21 |

FOREIGN PATENT DOCUMENTS

| 498696 | 2/1951 | Belgium | 3/27 |
|---|---|---|---|
| 883042 | 7/1953 | Fed. Rep. of Germany | 3/2 |
| 633838 | 2/1978 | France | 3/26 |
| 142338 | 5/1920 | United Kingdom . | |

Primary Examiner—Richard J. Apley
Assistant Examiner—David J. Isabella
Attorney, Agent, or Firm—Pollock, Vande Sande & Priddy

[57] ABSTRACT

A knee joint for an artificial limb comprises a knee member having a part spherical convex lower surface pivoted about an axis to a knee housing having a part spherical concave upper surface conforming to the curvature of the knee member. A spring loaded plunger directly connected to a release cable runs on a guideway on the curved surface of the knee housing when the knee is flexed and in the unflexed position latches into a seating to prevent knee flexion. A collet fixing is preferably used to attach the shin tube into a socket depending from the knee housing without the need to drill the tube.

12 Claims, 3 Drawing Figures

KNEE JOINT FOR ARTIFICIAL LIMBS

FIELD OF THE INVENTION

The present invention relates to a knee joint for a so-called primary artificial leg.

SUMMARY OF THE INVENTION

The invention provides a knee joint for an artificial leg which is of mechanically simple construction but is nevertheless durable and effective and which comprises a knee member having a part spherical convex lower surface pivoted about an axis to a knee housing having a part spherical concave lower surface conforming to that of the knee member, the knee member having a spring-loaded locking plunger posterior to the pivot axis and having a generally vertical line of action which in flexed positions of the joint travels over and is supported in a retracted position by the part spherical surface of the knee housing or by a guideway formed therein or thereon and in the unflexed position thereof latches into a seating to prevent flexion of the joint.

The knee joint permits the use of an endoskeletal shin casting which is of modular construction and the knee member which is of wood and is connected to a stump socket can readily be adapted to the requirements of a particular patient. Thus it combines the traditional artificial limb technology in wood above the knee with the more modern modular endoskeletal technology for the part of the limb below the knee and enables limbs that are simple in construction and light in weight to be made.

DESCRIPTION OF PREFERRED FEATURES

In an advantageous construction a rib upstanding from the curved top surface of the knee housing defines a guideway leading to the socket that is defined in a spigot upstanding from said curved surface, the anterior face of the spigot cooperating in the unflexed position of the joint with an extension stop in the concave lower surface of the knee member to define the unflexed position of the joint. The socket in the spigot intrudes into or closely approaches the envelope of curvature of the knee member, the knee member is relieved behind the extension stop to avoid interference with the spigot as the joint unflexes, and the plunger is arranged so that its position of maximum extension does not substantially protrude beyond the envelope of curvature of the knee member. With this arrangement the joint cannot become accidentally locked in the fully flexed state by entrapment of the locking plunger with the top anterior surface of the knee housing, and the extension stop is concealed between the knee member and the knee housing throughout substantially the whole angular range of travel of the knee. A top posterior portion of the spigot preferably defines a flexion stop face that abuts part of the knee member to define a fully flexed state of the joint.

Preferably there is provided a demountable fastening in the shin member by which it may be clamped onto a shin tube. Such a joint comprises a socket defined by a main bore in which the shin tube is received, an auxiliary bore directed perpendicular to the axis of the main bore and intersecting it over a small arc, first and second collets which fit in the auxiliary bore and have bearing faces shaped to conform to the curvature of the shin tube, and clamping bolt means for urging the first and second collets together so that they press on the shin tube and retain it in the socket. The demountable joint combines manufacturing simplicity with ease of assembly and good fatigue life and has the particular advantage that the shin tube need not be weakened by drilling or slitting.

BRIEF DESCRIPTION OF THE DRAWINGS

An embodiment of the invention will now be illustrated in the accompanying drawings in which.

DESCRIPTION OF THE ILLUSTRATED EMBODIMENT

Figure 1:
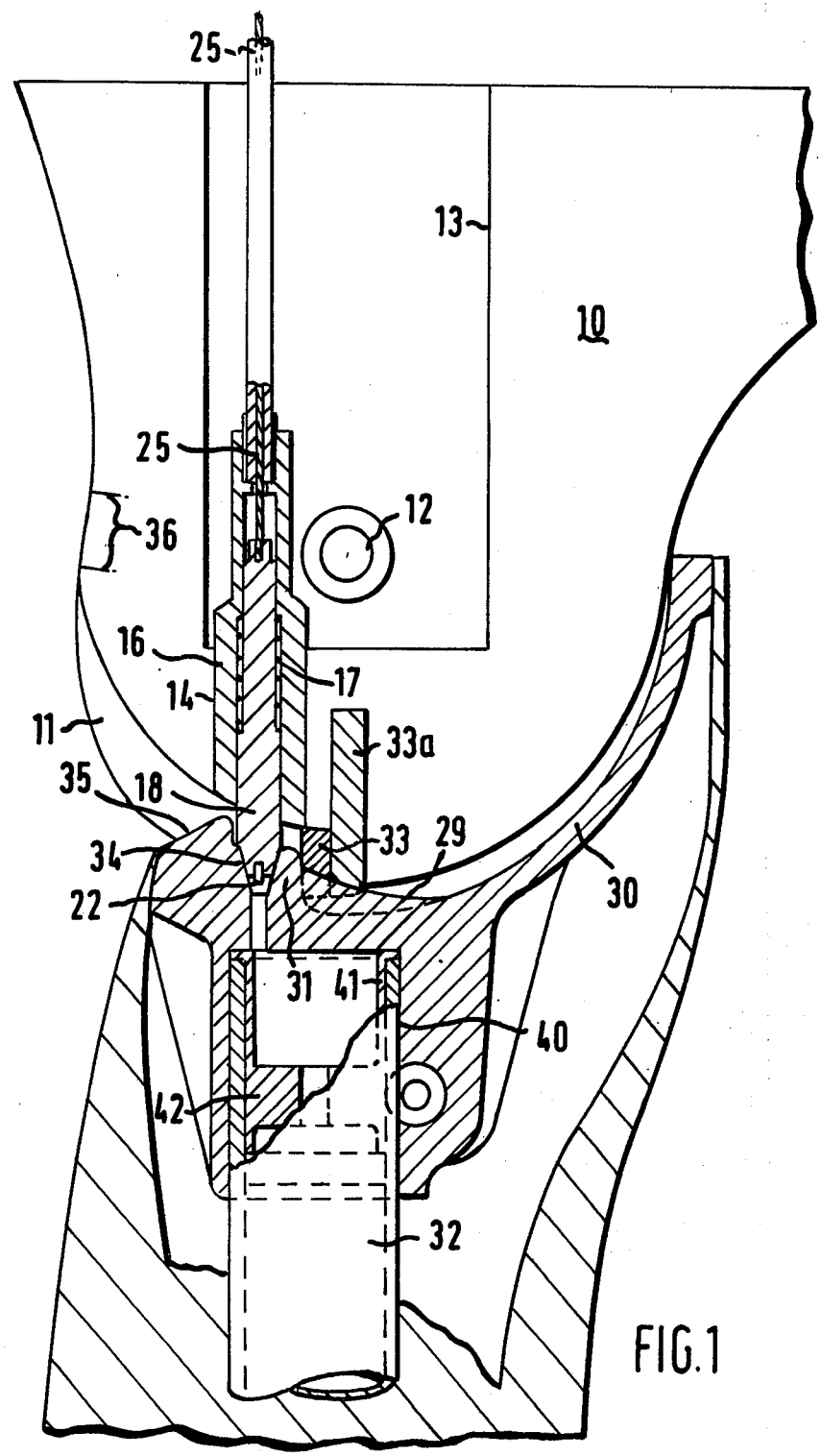
FIG. 1 shows in vertical section the region adjoining the knee of an artificial leg.

In FIG. 1 a thigh stump socket (not shown) is fixed to a knee member in the form of a shaped block 10 of wood, polyurethane foam or other conveniently worked material. The height of block 10 may be adjusted e.g. by cutting with a saw to meet the needs of an individual patient for whom the limb is intended. A relatively large vertical bore 13 from the top face of block 10 leads to a smaller bore 14 that opens through the lower face of the knee block which is part spherical at a position posterior of the position of knee bolt and bearings 12. An extension buffer 33 mounted on a plate 33a is let into the curved lower face of the knee member 10 below bolt 12 as viewed, partially in phantom in FIG. 1. The portion of the block 10 posterior of the extension buffer 33 is formed with a channel 11 or is otherwise relieved, and a plunger 18 in housing 16 is mounted in the bore 14 so that it has a vertical line of action and its tip in its position of maximum downward extension projects beyond the relieved portion of the block surface but not significantly beyond the envelope of curvature of the lower face of the block. By this means, as will become apparent below, the tip of the plunger cannot latch onto the top anterior edge of the knee socket and thereby accidentally lock the knee in a fully flexed or hyperflexed state. Plunger 18 is urged downwardly by coil spring 17 in housing 16, has bearing portions towards its upper and lower ends that slideably guide it in the housing for vertical movement and is directly connected at its upper end to Bowden cable 25 which may be pulled upwardly to release the joint. Plunger 18 has a conical tip provided with an anti-friction pip 22 of Teflon or like material.

The knee housing 30 may be a casting in light alloy or an injection moulding in glass filled nylon and is pivoted to the knee member by bolt 12. Its upper face presents a part spherical concave surface conforming generally to the curvature of the lower face of the knee member. It is supported on a pylon tube 32 to which it is connected by a demountable compression joint described below. The upper face of the housing 30 is formed with an upstanding rib 29 whose curved top face forms a smooth track or cam surface leading to a spigot 31 also upstanding from the top face of the housing 30 at a posterior location. The track defined by rib 29 leads to a frustoconical seating or socket 34 into which the tip of plunger 18 locates when the knee and shin portions of the leg are in the unflexed position shown. By this means the plunger and seating automatically take up wear so that the knee has no play in its unflexed locked state that would be damaging to patient confidence. The knee is locked both against flexion and against overextension by the plunger 18. Pulling on cable 25 directly raises and disengages plunger 18 from socket 34 after which anti-friction pip 22 travels over the top face of rib 29 as the knee flexes, the said rib either supporting the plunger in its retracted position or allowing it to extend as the knee flexes and camming it towards its retracted position as the knee is unflexed. The extension buffer 33 and backing plate 33a are formed with notches, as shown in phantom in FIG. 1, to accommodate the rib 29 as the knee is unflexed. The unflexed position of the knee is further defined by abutment of the anterior face of spigot 31 with the extension buffer 33. The arrangement has the advantage that the extension buffer 33 is removed from its normal position in the anterior face of the knee member 11 where clothing is prone to catch between itself and the top anterior edge of knee housing 30 but instead the extension buffer 33 is concealed by housing 30 throughout substantially the whole of its range of travel. At the fully flexed position of the knee, flexion stop 35 on the top posterior surface of spigot 31 contacts portion 36 on the knee member 10 to prevent hyperflexion of the knee. As the knee is returned from the flexed to the straight position the plunger 18 travels back over the top face of rib 29 and automatically latches back into the seating or socket 34.

Figure 2:
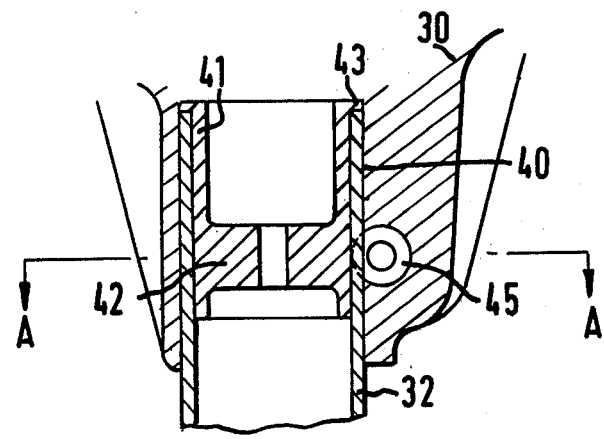
FIG. 2 is a view in vertical section of a demountable fastening for fixing the shin tube into the socket of the shin member in the artificial leg of FIG. 1.
Figure 3:
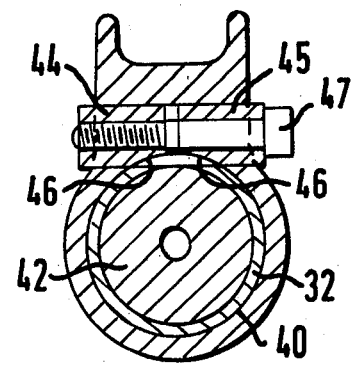
FIG. 3 is a view of the joint in horizontal section on the line A—A of FIG. 2.

In FIG. 2, the upper end of a shin pylon tube 32 is a push fit in a socket 40 defined by a vertical bore in the lower face of knee housing 30. A reinforcing insert 41 is a push fit in the top of tube 32. It is formed towards its lower end with a horizontally directed reinforcing annulus 42 which is capable of withstanding high compressive loads and at its top with an outwardly directed locating flange 43 which acts as an abutment for the top end of the tube 10. As more clearly seen in FIG. 3 the socket 40 is formed with a horizontal bore that intersects the vertical bore in which tube 32 fits over a small arcuate portion thereof. A pair of collets 44, 45 fit into the horizontal bore, one of them 45 having a plain through-hole and the other 44 having a threaded through hole. Each collet has a shaped bearing surface 46 conforming to the curvature of the outer surface of the tube 32 which can only be inserted fully home in the socket 40 when the bearing surfaces 46 are appropriately positioned. It will be noted that in the assembled joint the horizontal bore registers with the reinforcing annulus 42 of the insert 41. A clamping bolt 47 is inserted through collet 45 into collet 44 in which it is threadedly located.

I claim:
1. A knee joint for an artificial leg, comprising:
an upper knee member having a part spherical convex lower surface;
a lower knee housing having a part spherical concave upper surface conforming to that of said knee member;
means pivotally securing said knee member and said knee housing together for flexion about a knee pivot axis;
a locking plunger in said knee member located posterior to said axis and having a generally vertical line of action, said plunger being slideably guided in a bore in said knee member, said bore opening to the lower face thereof, for movement between one position in which the tip of said plunger protrudes from said bore and another position in which said tip of said plunger is retracted into said bore, resilient means biasing said locking plunger towards its extended position;
a spigot in said knee housing having means defining a socket therein that is raised from said part spherical concave upper surface and is aligned with said plunger when the knee joint is unflexed; and
means defining a cam surface upstanding from said part spherical concave upper surface of said knee housing, said cam surface leading from said upper surface to said spigot and aligned with said plunger when the knee joint is partly flexed so that as the knee joint is straightened from its fully flexed position, said tip of said plunger travels over and is retracted by said cam surface against the action of said spring and when the knee joint is unflexed said tip snaps into said socket with which it is maintained in latching engagement by said spring to prevent unintentional flexion of the knee joint.

2. A knee joint according to claim 1, wherein said socket in said spigot closely approaches the envelope of curvature of said knee member; the anterior face of said spigot cooperates in the unflexed position of the knee joint with an extension stop in the concave lower surface of said knee member to define the unflexed position of the joint; said knee member is relieved behind said extension stop to avoid interference with said spigot as the knee joint unflexes; and said plunger is arranged so that its position of maximum extension does not substantially protrude beyond the envelope of curvature of said knee member.

3. A knee joint according to claim 2, wherein a top posterior portion of said spigot defines a flexion stop face that abuts part of said knee member to define a fully flexed state of the knee joint.

4. A knee joint according to claim 3, wherein said knee member is of wood and said knee housing is of glass filled nylon.

5. A knee joint according to claim 1, wherein said plunger is slideably guided in a housing in said bore in said knee member and said resilient means comprises a coil spring within said housing between said plunger and the inner housing surface, said coil spring having a vertical line of action.

6. A knee joint according to claim 1, wherein said tip of said locking plunger is formed with a low-friction member to facilitate its travel over said cam surface.

7. A knee joint according to claim 1, wherein said locking plunger is directly connected to a Bowden cable.

8. A knee joint according to claim 1, wherein a further socket depending from said knee housing is defined by a main bore, an auxiliary bore is directed perpendicular to the axis of said main bore and intersects it over a small arc, first and second collets fit in said auxiliary bore and have bearing faces shaped to conform to the curvature of a tubular member and clamping bolt means urge said first and second collets together so that they press on said tubular member and retain it in said further socket.

9. A joint according to claim 8, further comprising a reinforcing insert in the end of said tubular member formed with means registering with said collets for resisting compressive loads on said tube.

10. A knee joint according to claim 2, wherein said socket in said spigot intrudes into the envelope of curvature of said knee member; the anterior face of said spigot cooperates in the unflexed position of the knee joint with an extension stop in the concave lower surface of said knee member to define the unflexed position of the joint; said knee member is relieved behind said extension stop to avoid interference with said spigot as the knee joint unflexes; and said plunger is arranged so that its position of maximum extension does not substantially protrude beyond the envelope of curvature of said knee member.

11. A knee joint according to claim 10, wherein a top posterior portion of said spigot defines a flexion stop face that abuts part of said knee member to define a fully flexed state of the knee joint.

12. A knee joint according to claim 11, wherein said knee member is of wood and said knee housing is of glass filled nylon.

* * * * *